(12) United States Patent
Kaplan et al.

(10) Patent No.: US 7,176,033 B2
(45) Date of Patent: Feb. 13, 2007

(54) INCREASED SENSITIVITY OF PEPTIDE DETECTION WITH MATRIX-ASSISTED LASER DESORPTION/IONIZATION MASS SPECTROMETRY BY IN VACUO METHYLATION OF AMINO GROUPS

(76) Inventors: Harvey Kaplan, 432 Crestview Road, Ottawa, Ontario (CA) K1H 5G9; Nicolas Stewart, 245 Allbirch Road, R.R. 1, Woodlawn, Ontario (CA) K0A 3M0

( * ) Notice: Subject to any disclaimer, the term of this patent is extended or adjusted under 35 U.S.C. 154(b) by 546 days.

(21) Appl. No.: 10/392,173

(22) Filed: Mar. 20, 2003

(65) Prior Publication Data

US 2003/0180962 A1    Sep. 25, 2003

(51) Int. Cl.
    *G01N 33/00* (2006.01)
(52) U.S. Cl. .................................................. 436/86
(58) Field of Classification Search ................ 436/86
    See application file for complete search history.

(56) References Cited

U.S. PATENT DOCUMENTS 5,273,886 A * 12/1993 Aswad ..................... 435/15

OTHER PUBLICATIONS

Johnson et al. "Formation of Isoaspartate at Two Distinct Sites during in Vitro Aging of Human Growth Hormone" Journal of Biological Chemistry, vol. 264, No. 24, 25(14262-14271)(1989).*

* cited by examiner

*Primary Examiner*—Monique T. Cole
(74) *Attorney, Agent, or Firm*—Dimock Stratton LLP; Adrian M. Kaplan

(57) ABSTRACT

The invention relates to a method of detecting peptides having amino groups. The method involves digesting a protein into at least two peptides having an amino group. The amino groups are trimethylated under vacuum and then the peptides are detected using mass spectrometry. Another embodiment of the invention provides a method of detecting peptides. The method employs a protein having a lysine residue having an ε-amino group. The protein is digested into at least two peptides. The ε-amino group is then trimethylated under vacuum. The peptides are then detected using mass spectrometry. The method can also be used for a protein having an α-amino group. Alternatively, a method of detecting peptides is provided for a protein having a lysine residue where the lysine residue has an ε-amino group. The protein is digested into at least two peptides having an α-amino group. The α-amino group and ε-amino group are trimethylated under vacuum and the peptides are detected using mass spectrometry.

11 Claims, 8 Drawing Sheets

INCREASED SENSITIVITY OF PEPTIDE DETECTION WITH MATRIX-ASSISTED LASER DESORPTION/IONIZATION MASS SPECTROMETRY BY IN VACUO METHYLATION OF AMINO GROUPS

FIELD OF THE INVENTION

The invention relates to a method of detecting peptides using mass spectrometry.

BACKGROUND OF THE INVENTION

The elucidation of the human and other genomes (1,2) has spurred efforts to identify proteins expressed by cells in various tissues, i.e. the proteome. Matrix-assisted laser desorption/ionization (MALDI) mass spectrometry (MS) is one of the major tools being employed for the analysis of peptides generated by enzymatic digestion of expressed proteins. Trypsin is the most commonly used enzyme because the predictability of its cleavages facilitates identification of proteins by database searching. A difficulty encountered with this strategy is that there is a great variability in the signal intensity for peptide depending on their composition. In many cases peptides which are known to be generated are not detected. It has been observed that the detection of arginine-containing peptides is much more sensitive than lysine-containing peptides (3). Conversion of lysine residues in peptides to homo-arginine by guanidinylation has been shown to increase the sensitivity of detection of these peptides (4,5,6). The reason for this increased sensitivity is not fully understood and the use of guanidinylation for increasing the sensitivity of MALDI peptide detection is based only on an empirical observation. A severe limitation of this approach is that it is applicable only to peptides containing lysine. In enzymatic digests, other than trypsin, the majority of the peptides are not lysine peptides and this methodology is not applicable.

In vacuo reaction of amino groups with iodomethane in proteins or peptides produces a trimethylated quaternary ammonium derivative with a permanent positive charge (7,8,910). There is no known theory that predicts that this derivatization would increase the sensitivity of detection of peptides by MALDI MS. However, this possibility has never been tested primarily because iodomethane has not been used for chemical modification of peptides or proteins in aqueous solution due to its low solubility in water. Currently, modification procedures are carried out under aqueous conditions that require several manipulative procedures. In vacuo trimethylation requires only one step and is easier to carry out than modification procedures under aqueous conditions. In addition it has several other significant technical advantages:

1) It requires no solvent removal, clean-up steps or any other manipulation prior to preparing the sample for mass spectrometric analysis.
2) Methylation can be carried out on much smaller amounts of peptide or protein than a solvent-based modification procedure such as guanidinylation.
3) Very small amounts of reagent are required which permits the cost effective use of isotopically enriched ($^{13}C$, $^{14}C$, $CD_3$ $CT_3$) reagent for special applications.
4) Guanidinylation can only be carried out on $\epsilon$-amino groups whereas methylation can be carried out on both $\alpha$-amino and $\epsilon$-amino groups.
5) The in vacuo methylation can be used to differentiate between peptide and non-peptide material greatly simplifying the interpretation of the mass spectra. There is therefore a need for a method of detecting a peptide using mass spectrometry that involves in vacuo trimethylation of the peptide.

SUMMARY OF THE INVENTION

The invention is the use of the in vacuo reaction of peptides and proteins with iodomethane to generate peptides with timethyalted $\alpha$-amino groups or peptides with trimethylated $\epsilon$-amino groups to increase the signal intensity of peptides in MALDI MS.

The increase in signal intensity in most cases is at least an order of magnitude and allows for the detection of peptides that previously could not be detected by mass spectroscopy. Another useful advantage of the in vacuo methylation procedure is that trimethylation of a peptide amino group can be carried out readily with a combination of isotopes $^{13}CH_3I$ and $^{12}CH_3I$ or $CD_3I$ and $CH_3I$, yielding a doublet signal either 3 or 9 units apart, respectively. The presence or absence of such a doublet signal can be used as a criterion to discriminate between peptide and non-peptide signals in the mass spectrum. As spectra often contain non-peptide impurities this ability to use isotope double-labelling greatly facilitates the detection of peptides.

The invention provides a method of detecting peptides using mass spectrometry including the step of trimethylating certain groups of the peptide under vacuum.

According to one aspect of the present invention, there is provided a method of detecting peptides having amino groups, said method comprising the following steps:
  providing a protein;
  digesting the protein into at least two peptides having an amino group;
  trimethylating said amino groups under vacuum; and
  detecting said peptides using mass spectrometry.

According to another aspect of the present invention, there is provided a method of detecting peptides comprising the following steps:
  providing a protein having a lysine residue, said lysine residue having an $\epsilon$-amino group;
  digesting the protein into at least two peptides;
  trimethylating said $\epsilon$-amino group under vacuum; and
  detecting said peptides using mass spectrometry.

According to another of the present invention, there is provided a method of detecting peptides comprising the following steps:
  providing a protein having a lysine residue, said lysine residue having an $\epsilon$-amino group;
  digesting the protein into at least two peptides having an $\alpha$-amino group;
  trimethylating said $\alpha$-amino group and $\epsilon$-amino group under vacuum; and
  detecting said peptides using mass spectrometry.

According to yet another aspect of the present invention, there is provided a method of detecting peptides comprising the following steps:
  providing a protein having an amino group;
  trimethylating said amino group under vacuum;
  digesting the protein into at least two peptides; and
  detecting said peptides using mass spectrometry.

According to another aspect of the present invention, there is provided a method of detecting peptides comprising the following steps:
  providing a protein having an $\alpha$-amino group;
  digesting the protein into at least two peptides; and detecting the peptides having a trimethylated α-amino group using mass spectrometry.

DETAILED DESCRIPTION OF THE PREFERRED EMBODIMENTS

Materials and Methods

Materials

Figure 1:
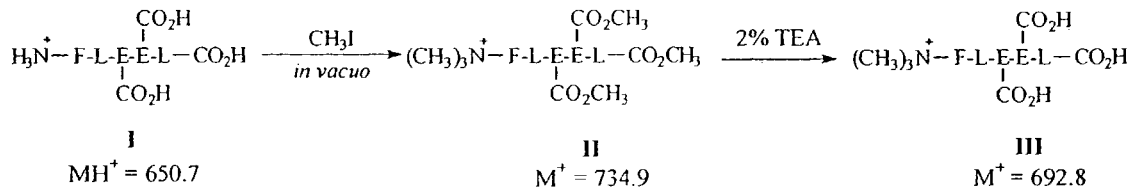
FIG. 1 depicts a reaction scheme and products with predicted monoisotopic masses from reaction of iodomethane with test peptides.
Figure 1:
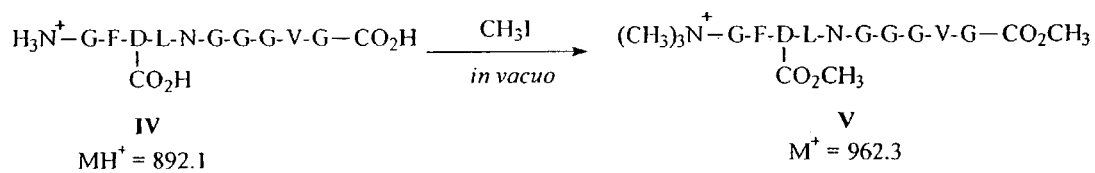
Figure 1:
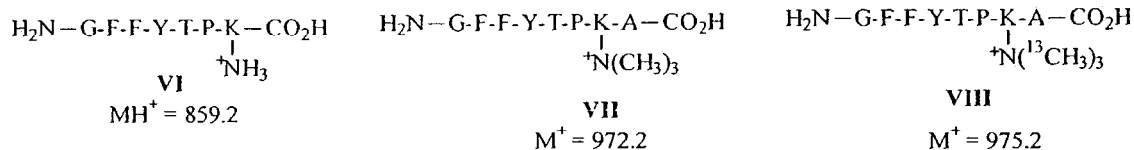
Figure 1:
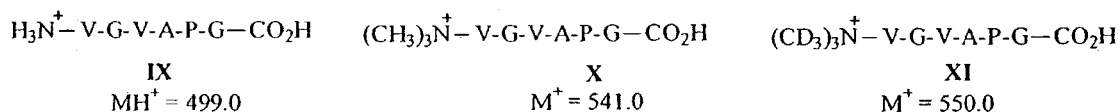

Oxidized B chain from bovine insulin (81% pure), Human Hemoglobin and FLEEL, GFDLNGGGVG and VGVAPG peptides were obtained from Sigma and used without further purification. Allostatin 3 ($NH_3^+$-GGSLYSFGL-$CONH_2$) and dermorphin ($NH_3^+$-YAFGYPS-$CONH_2$) peptides were purchased from Bachem and used without further purification. Iodomethane was purchased from BDH and [$^{13}$C] iodomethane 99 atom % was obtained from Aldrich. Papain, trypsin from bovine pancreas and N-tosyl-λ-phenylalanine chloromethyl ketone (TPCK) were purchased from Sigma.

Methylation of Peptides

In vacuo methylation with iodomethane was carried out as previously described[7-10] with the minor modifications described below. A sample of peptide (0.1 mg) dissolved in 100 μL of 10 mM tetramethylammonium phosphate (pH 8.0) was lyophilized in small glass conical vials (13×45 mm). The vial containing the lyophilized peptide sample was placed in a larger glass tube (15×100 mm). After forming a narrow constriction near the upper portion of the outer tube with a flame, the lower portion of the tube was placed in liquid nitrogen and iodomethane (30 μL) was introduced under a dry nitrogen atmosphere. The tube was evacuated (ca. 70 mTorr) and sealed under vacuum at the constriction. The sealed tubes were placed in a mineral oil block heater at 75° C. for 18 h. The reaction was stopped by trapping out the excess reagent at the top of the tube with a jacket filled with liquid nitrogen fitted over the tube. The top of the glass tube was scored and the vacuum released by breaking the glass tube at the score mark. The inner glass tube containing the methylated peptide was removed.

Removal of Methyl Esters

After completion of the in vacuo methylation procedure, the sample was dissolved in 100 μL of 2% triethylamine (TEA), transferred to a micro-centrifuge tube, heated in a water bath for 1 hour at 90° C. and then dried under a vacuum using a Speed-Vac apparatus.

Methylation Oxidized B Chain of Insulin

Three separate samples each containing (0.86 mg, ca. 200 nmol) of oxidized B chain of insulin in 100 μL 2% TEA were lyophilized in small glass tubes. In vacuo methylation was performed with $CH_3I$ and $^{13}CH_3I$ as described above using the tubes with the lyophilized samples in inserts. As a control, the oxidized B chain was heated without iodomethane.

After in vacuo methylation, methyl esters were removed by the procedure described above. Samples were left to cool to room temperature. Aliquots (50 μL) were transferred to micro-centrifuge tubes and neutralized with 5 μL 5% formic acid. Samples containing equal amounts of untreated and $^{12}$C-methylated oxidized B chain and, $^{12}$C and $^{13}$C methylated oxidized B chain, were also prepared.

Trypsin Digestion

TPCK trypsin was prepared as previously described.[12] A stock solution of TPCK trypsin was prepared as follows: 5 μL 1M $CaCl_2$, 2.0 mL 200 mM $NH_4HCO_3$ and 50 μL 5 mg/mL of TPCK trypsin. An aliquot (100 μL) of this stock was added to each of the oxidized B chain samples (ca. 50:1 w/w; B chain to enzyme), digestion was carried out for 1 h at 37° C. in a shaker bath. Samples were dried using a speed-vac centrifuge apparatus, dissolved and dried from 20 μL dd$H_2$O and then dissolved and dried from 10 μL 5% formic acid prior to MS.

Methylation Human Hemoglobin and Digestion with Papain

A 5.0-ml solution of 1% human hemoglobin in 10 mM tetramethylammonium phosphate (pH 8.0) was prepared. Two 100 μL aliquots each containing 1.0 mg (ca. 150 nmol) of hemoglobin were lyophilized in small glass tubes. In vacuo methylation was performed with $CH_3I$ and $CD_3I$ as described above using the tubes with the lyophilized samples in inserts. The methylated samples were dissolved in 500 μL of 100 mM pyridine-acetate buffer pH 6.5. A solution of papain (10 μL) in 100 mM pyridine-acetate buffer pH 6.5 containing 0.05 mg of papain was added and digestion was carried out for 1 h at 37° C. Samples were dried using a speed-vac centrifuge apparatus, dissolved and dried from 20 μL dd$H_2$O and then dissolved and dried from 10 μL 5% formic acid prior to MS.

MALDI MS

Figure 4:
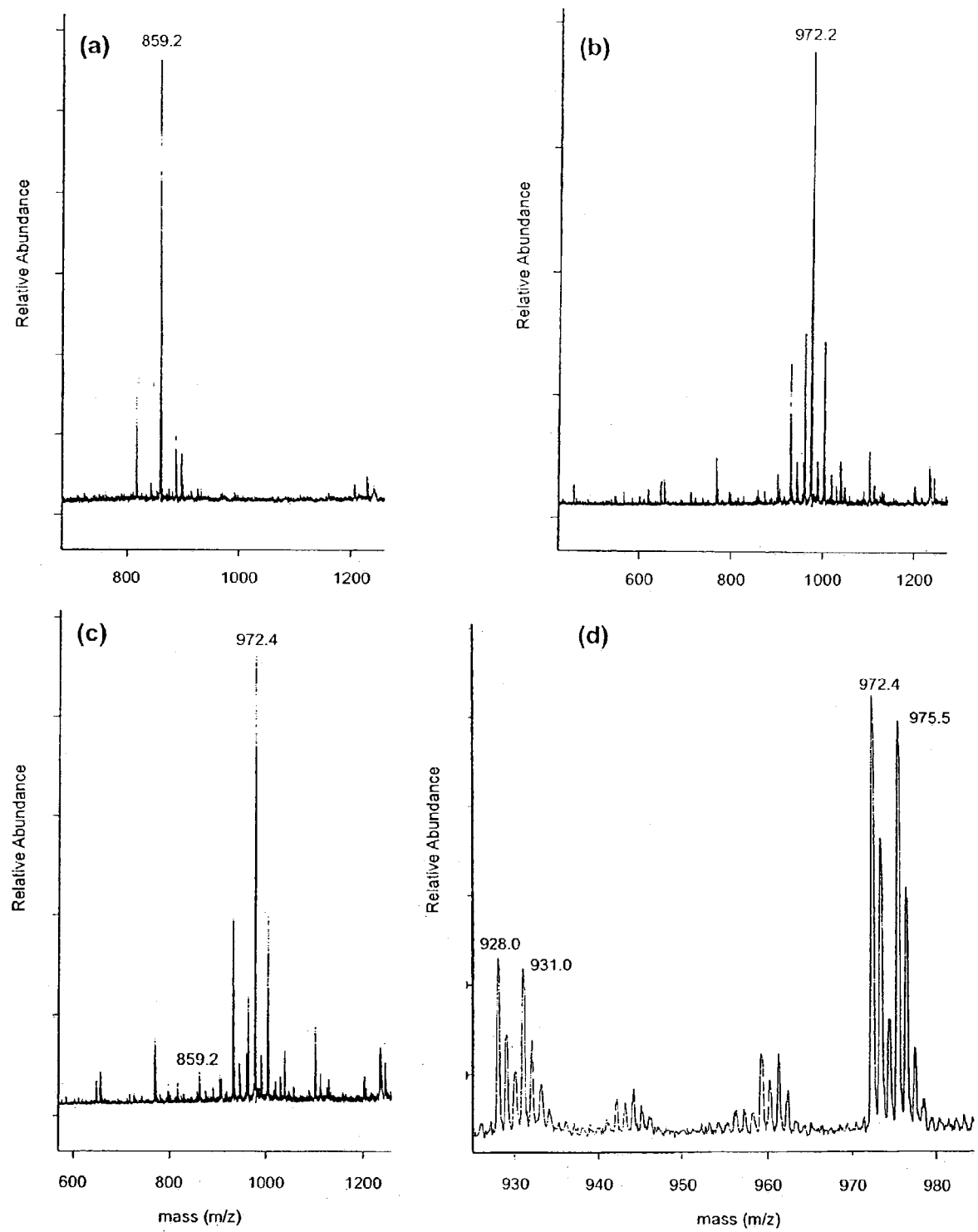
FIG. 4 shows a portion of MALDI-TOF spectra of 10 pmol of trypsin digest of (a) unmodified oxidized insulin B-chain (b) in vacuo methylated oxidized insulin B-chain (c) equimolar mixture of methylated and unmodified oxidized insulin B-chain and (d) expanded spectrum of an equimolar mixture of $^{12}$C-methylated and $^{13}$C-methylated oxidized insulin B-chain.

Samples were dissolved in an appropriate volume of 5% formic acid (10-100 μL) and dried under vacuum using a Speed-Vac apparatus. Samples were prepared for MALDI-TOF MS by dissolving in 0.1% trifluoroacetic acid and mixing with the matrix, α-cyano 4-hydroxy cinnamic acid (3 mg dissolved in 300 μL of acetonitrile+ethanol (1:1)). The spectra in FIG. 4 were obtained using a PerSeptive Biosystems Voyager-Elite MALDI-TOF mass spectrometer; all other spectra were obtained on a Micromass TofSpec-2E MALDI-TOF MS.

Results and Discussion

The reaction scheme for the test peptide FLEEL with iodomethane is shown in FIG. 1. In vacuo reaction of I with iodomethane trimethylates the α-amino and also methylates the α-carboxyl of leucine, and the γ-carboxyl groups of glutamic acid to give II[2-4]. However, the methyl esters are easily removed by heating at 90° C. in base (2% TEA) to leave only III, the trimethylated α-amino derivative of the peptide.

Figure 2:
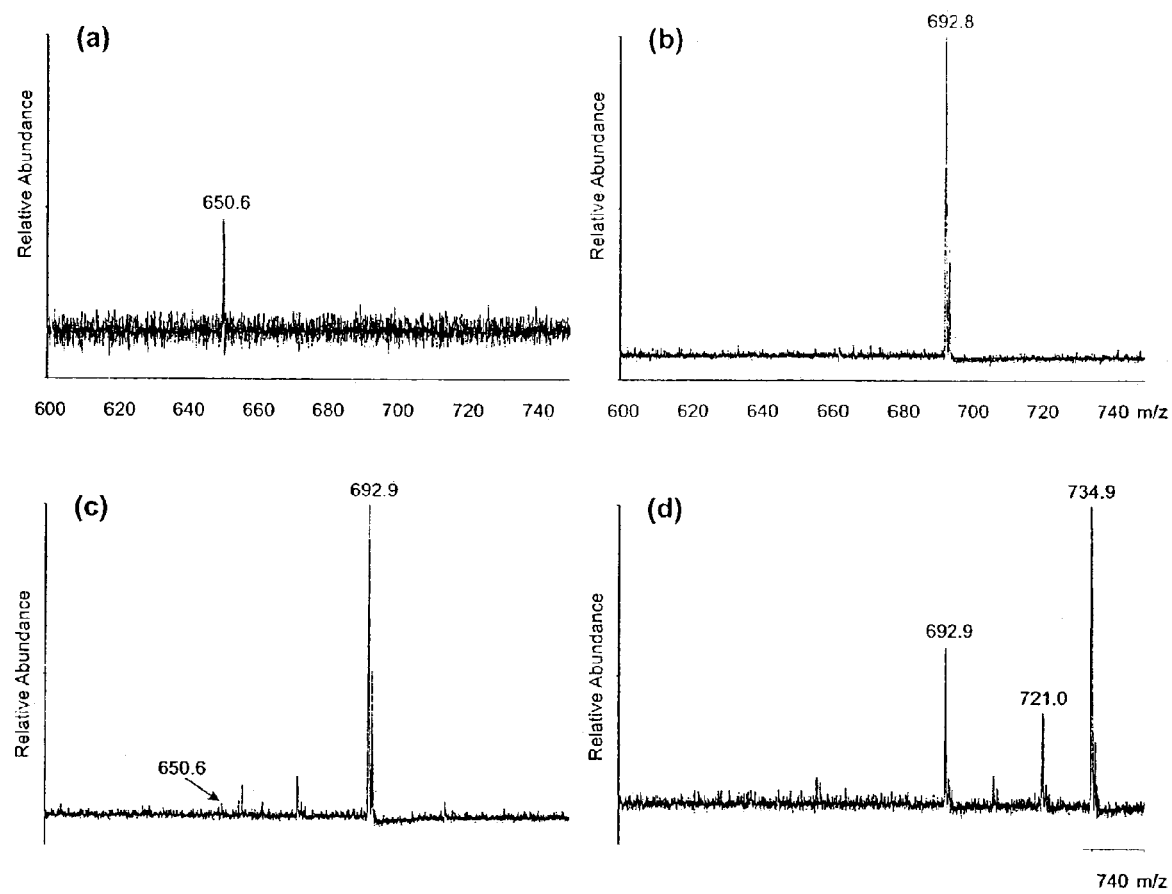
FIG. 2 shows a MALDI-TOF spectra of (a) 50 pmol of I (b) 10 pmol of III (c) mixture of 10 pmol of I and 10 pmol of III and (d) mixture of 10 pmol of II and 10 pmol of III.
Figure 3:
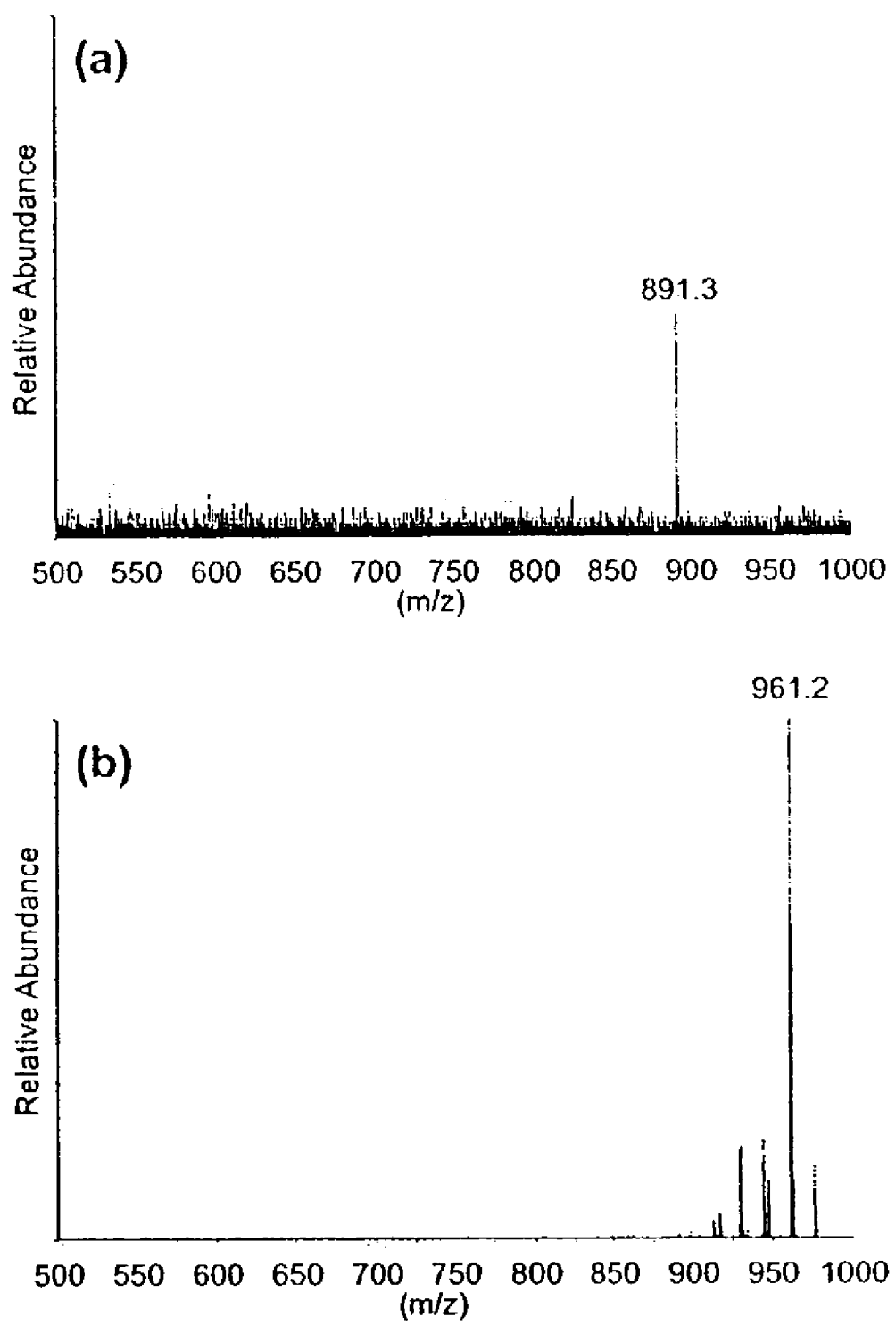
FIG. 3 shows a MALDI-TOF spectra of (a) 50 pmol of IV and (b) a mixture of 5 pmol of IV and 5 pmol of V.

The effect of methylation of the α-amino group on the sensitivity of MALDI detection of I is shown in FIG. 2. When equal amounts, viz. 10 pmols, of I and III are subjected to MALDI MS, the sensitivity of detection of the trimethylated α-amino derivative (III) is found to be much greater than the underivatized peptide with the protonated ammonium group (I) FIG. 2(c). Comparison of the MALDI MS on equal amounts of the tri-esterified derivative (II) and the corresponding derivative in which the ester groups have been converted to carboxyls (III) shows that the esterified derivative is detected with approximately twice the sensitivity of the non-esterified derivative. FIG. 2(d). Some of the di-ester derivative ($[M]^+=721.0$) is also present probably arising from a small amount of hydrolysis occurring during sample preparation for MS. In the case of peptide IV, the methylated derivative is readily detected at the 5 pmol level while the unmodified peptide is not detectable FIG. 3(b). Some minor impurities are also visible after methylation which are not detected in the untreated sample FIG. 3(a). As the peptide was employed as received from the supplier without further purification, it is likely that these are peptide impurities whose sensitivity of detection is also enhanced by reaction with iodomethane.

In order to test the effect of trimethylating the ε-amino of lysine on the sensitivity of MALDI detection, lyophilized oxidized B-chain of insulin was reacted in vacuo with iodomethane and digested with TPCK-treated bovine trypsin. The insulin B chain consists of 30 amino acids with one arginine at position 22 and one lysine at position 29. It is predicted that trypsin digestion will generate peptide VI ($[MH]^+=859.2$) and the derivatized B-chain will generate peptide VII ($[M]^+=972.2$) as trypsin does not readily cleave peptide bonds at a trimethylated lysine[11]. The results shown in FIG. 4(a) and FIG. 4(b) confirm that these are indeed the peptides generated by trypsin digestion. When equal amounts of VI and VII are simultaneously subject to MALDI MS, it is seen that the peptide VII with the trimethylated ε-amino group has a much higher signal intensity. FIG. 4(c).

Since in the in vacuo methylation procedure with iodomethane there are no competing side reactions with water, very little reagent is required and it is possible to use isotopically labeled iodomethane in a cost-efficient manner. The use of two isotopes provides a means of differentiating signals of peptides from non-peptides 1 in the mass spectrum. If equal amounts of oxidized insulin B-chain are reacted with [$^{12}C$] and [$^{13}C$] iodomethane digested with trypsin and mixed together, it is expected that the ε-trimethylamino lysine peptide will show two signals three mass units apart. Such a case is shown in the expanded spectrum in FIG. 4(d) where the expected signals at 972.4 and 975.4 are observed confirming that a trimethylated peptide is present. Similarly the signals at 928.0 and 931.0 indicate the presence of another trimethylated peptide. However, the mass does not correspond to a possible trimethylated peptide from the insulin B-chain and it is likely a peptide impurity. The other signals present are not separated by three mass units and are therefore not peptides containing a trimethylated amino group.

Figure 5:
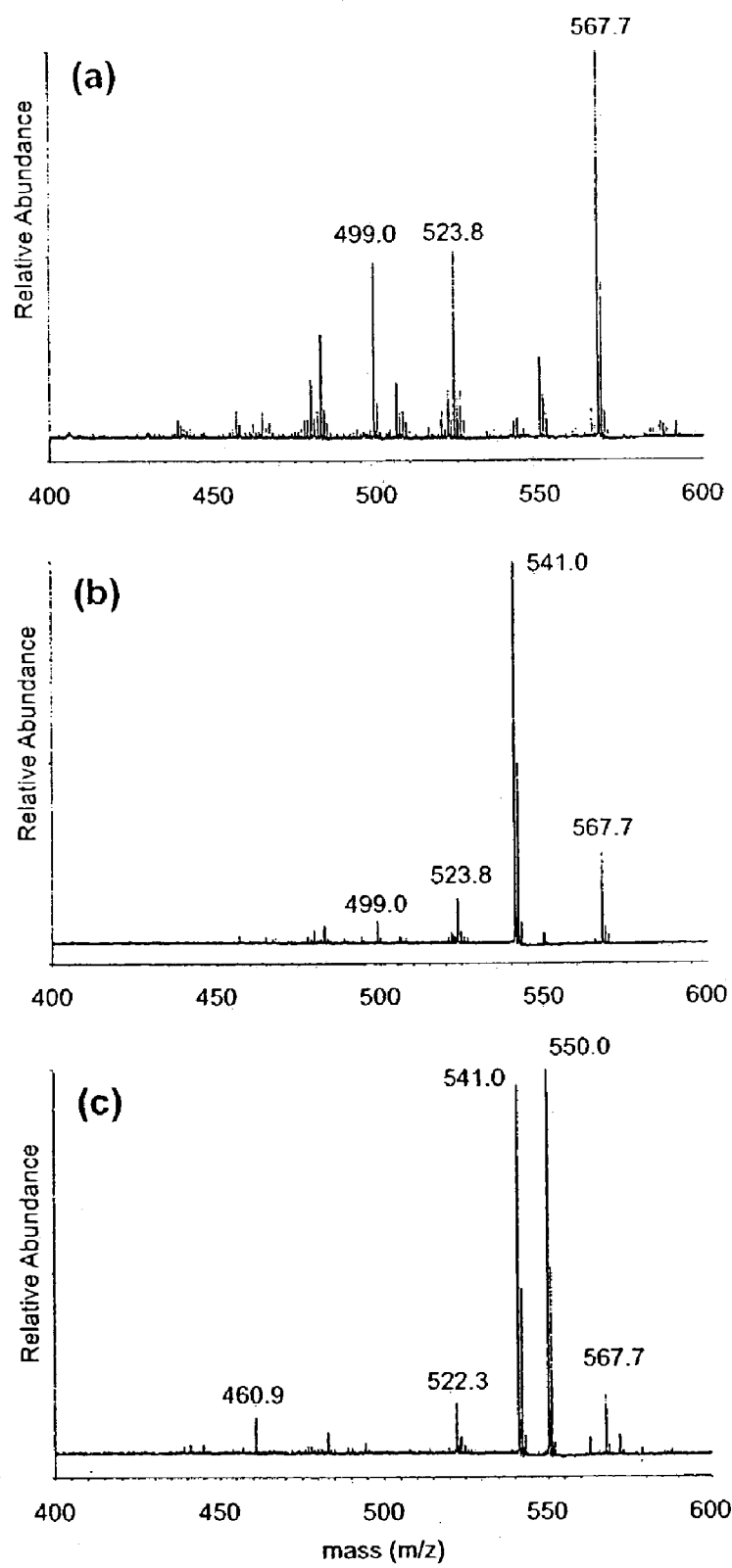
FIG. 5 shows a MALDI-TOF spectra of (a) 10 pmol of IX (b) a mixture of 10 pmol of IX and 10 pmol of X and (c) a mixture of 10 pmol of X and 10 pmol of XI.

In vacuo methylation with $CH_3I$ and $CD_3I$ can also be used to identify specifically signals in the mass spectrum arising from trimethylated peptides. The mass spectrum of IX has a signal with the expected mass at 499.0 mass units but several other signals are also present. FIG. 5(a). Without additional information, it is not possible to identify which of these signals corresponds to a peptide. The mass spectrum of a mixture of equal amounts of IX and X, the trimethylated α-amino derivative, gives the expected signal forty-two mass units higher at 541.0 mass units. Again, a large increase in signal intensity of at least an order of magnitude is observed for the trimethyl α-amino peptide FIG. 5(b). When equal amounts peptide X are reacted in vacuo with $CH_3I$ and $CD_3I$ and mixed, signals at 541.0 and 550.0 mass units are observed in FIG. 5(c), confirming that the signal at 449.0 mass units in FIG. 5(a) is from IX and that the other signals are due to non-peptide impurities.

Figure 6:
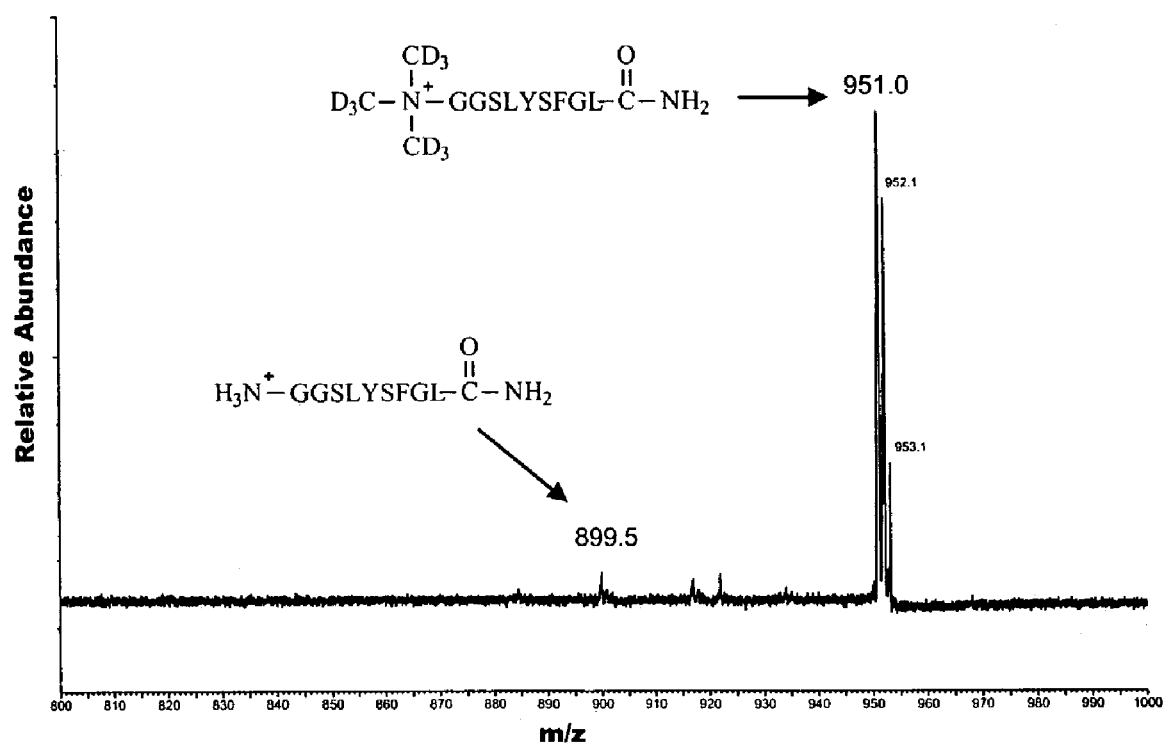
FIG. 6 shows a MALDI-TOF spectrum of a mixture of 1 pmol of the peptide Allostatin 3 ($NH_3^+$-GGSLYSFGL-$CONH_2$; $MH^+$=899.46) and 1 pmol its deutero trimethyl derivative (($CD_3)_3N^+$-GGSLYSFGL-$CONH_2$; $M^+$=950.57)
Figure 7:
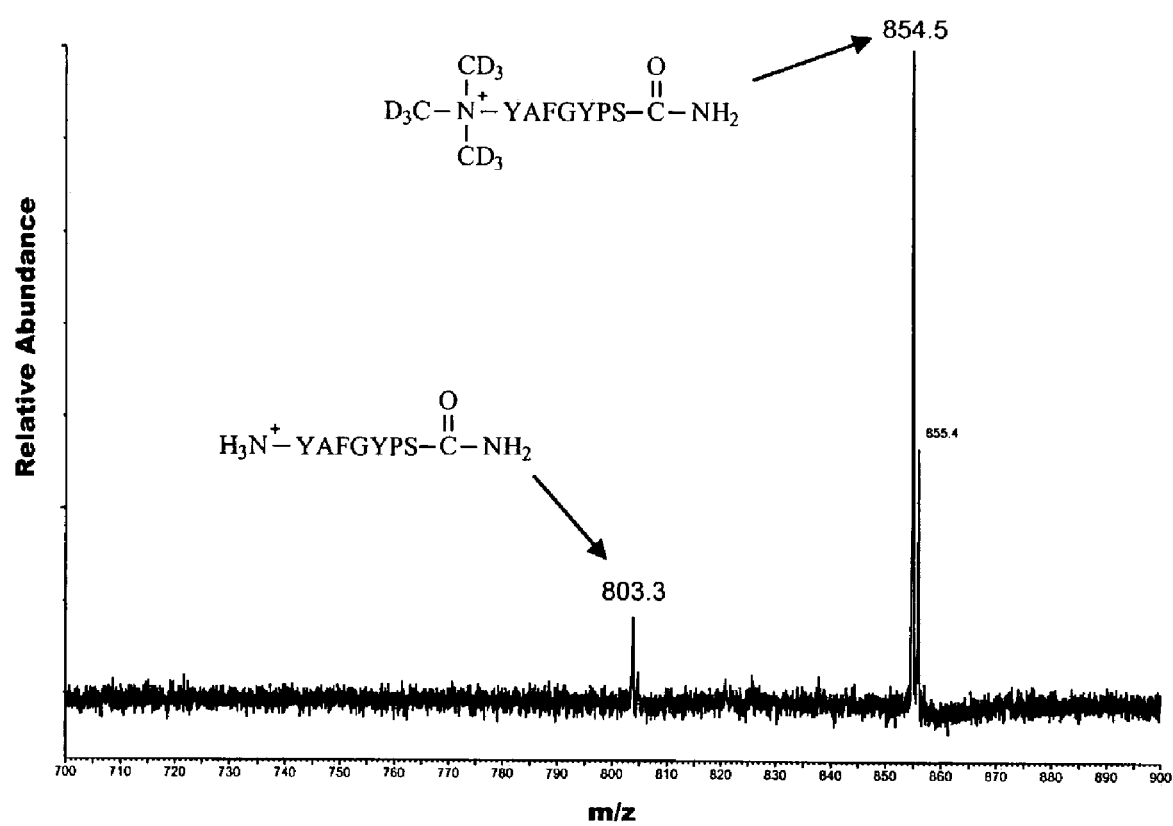
FIG. 7 shows a MALDI-TOF spectrum of a mixture of 1 pmol of the peptide Dermorphin ($NH_3^+$-YAFGYPS-$CONH_2$; $MH^+$=803.37) and 1 pmol its deutero trimethyl derivative ($(CD_3)_3N^+$-YAFGYPS-$CONH_2$; $M^+$=854.48))

All the peptides listed in FIG. 1 contain at least one free carboxyl group. Allostatin and dermorphin are peptides with an amidated carboxyl terminus and do not contain a free carboxyl group. The spectra in FIGS. 6 and 7 demonstrate that the trimethylated α-amino derivatives of these peptides also show a similar enhancement in the sensitivity of detection as peptides containing free carboxyl groups.

Figure 8:
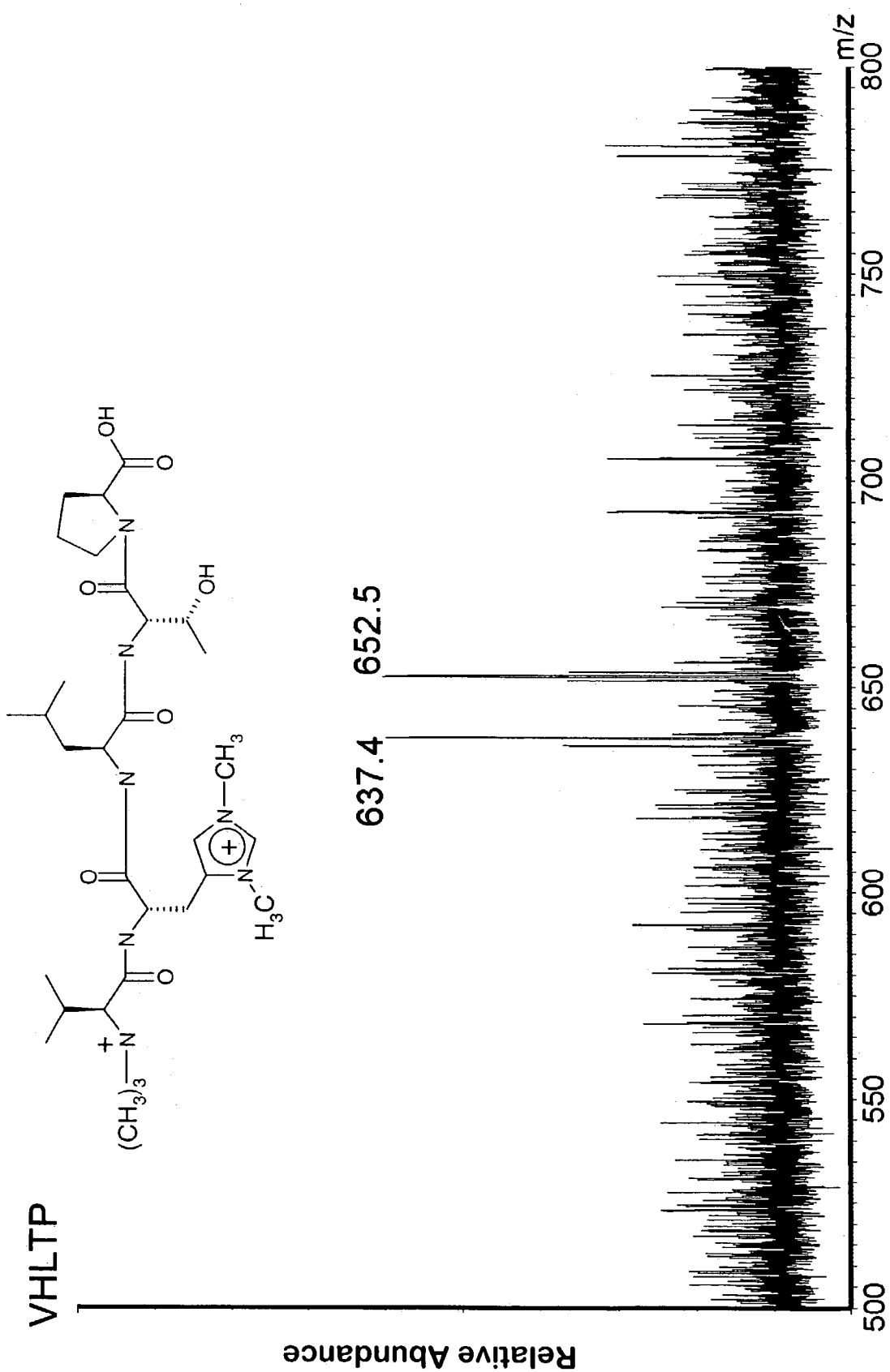
FIG. 8 shows the a MALDI-TOF spectrum of the total peptides from papain digest of mixture of 1 mg of $CH_3$-methylatated hemoglobin and 1 mg of $CD_3$-methylatated hemoglobin. The peaks at 637.4 mu and 652.5 mu correspond to the predicted monoisotopic masses for the pentamethyl derivatives ($CH_3$ and $CD_3$) for the known N-terminal sequence of the hemoglobin β-chain.

Hemoglobin was lyophilized at pH 8.0 and methylated in vacuo. Under these conditions the methylation reaction occurs predominantly with α-amino groups[9]. Therefore on digestion with a proteolytic enzyme only peptides derived from the N-terminus will contain a trimethylated α-amino group. Based on the discovery reported here that trimethylated α-amino peptides show a greatly enhanced MALDI sensitivity, it is expected that peptides with trimethyated α-amino groups would stand out when such a total enzymatic digest is subjected to MALDI MS analysis. FIG. 8 shows the MALDI spectrum obtained for 10 pmol of an equimolar mixture of in vacuo $CH_3$ and $CD_3$ methylated hemoglobins digested with papain. Two peaks at 637.4 mu and 652.5 differing by 15 mu stand out above the background of all the other peaks. The 15 mu difference indicates that 5 methyl groups have been incorporated into the peptide. In fact, the peak at 637.4 mu corresponds to the mass expected for the pentamethylated peptide $(CH_3)_3N^+$-VH$^+$$(CH_3)_2$ITP-COOH from the β-chain of hemoglobin. This peptide contains two permanent positive charges, one from the trimethylated α-amino group and one from the dimethylated imidazole function of the histidine residue. The observation that this peptide stands out in the MS spectrum demonstrates that doubly charged methyated peptides also have a greatly increased sensitivity in MALDI MS detection.

Vath et al.[13] reported that introduction of trimethylated quaternary ammonium into a peptide, viz. N-acetyl-Leu-enkephalin trimethylammonium ethyl ester, did not appear to improve the sensitivity of its detection with fast atom bombardment mass spectrometry (FABMS). If this is generally true for all such peptides using FABMS, then this is clearly in contrast with the results reported here using MALDI MS. The amount of trimethylated peptide used in obtaining the MALDI MS spectra presented in this communication varied from 5 to 20 pmol. It is evident from the results that these peptides could be readily detected at the 1 pmol level. After the in vacuo methylation procedure, the trimethylated peptides were loaded onto the target without any purification such as micro reverse phase columns that are commonly employed to remove salts. While a small amount of salt is present due to the in vacuo methylation procedure, such treatment does not appear to be necessary, but in some cases it may improve the quality of the spectra obtained.

CONCLUSIONS

The results obtained in the present study provide evidence that the introduction of a permanent positive charge in a peptide by trimethylation of an α- or ε-amino group can lead to substantial enhancement in the sensitivity of detection by MALDI MS. Further evidence of the generality of this observation was demonstrated by the observation that peptides without any free carboxyl groups or a peptide with two permanent positive charges also have a greatly increased sensitivity of detection by MALDI MS. The data obtained show such a significant increase in sensitivity leading to a conclusion that the MALDI detection of the vast majority of peptides generated by enzymatic digests could be significantly enhanced by the in vacuo methylation procedure.

From the foregoing, it will be appreciated that, although specific embodiments of the invention have been described herein for purposes of illustration, various modifications may be made without deviating from the spirit and scope of the invention.

REFERENCES 1. www.ncbi.nlm.nih.gov
2. www.expasy.org
3. Krause E, Wenschuh H, Jungblut P R. *Anal. Chem.* 1999;71: 4160.
4. Brancia F L, Oliver S G, Gaskell S J. *Rapid Commun. Mass Spectrom.* 2000; 14: 2070.
5. Beardsley R L, Karty J A, Reilly J P. *Rapid Commun. Mass Spectrom.* 2000;14:2147.
6. Hale J E, Butler J P, Knierman M D, Becker G W. *Anal Biochem.* 2000; 287: 110.
7. Taralp A, Kaplan H. *J. Prot. Chem.* 1977; 16: 183.
8. Kaplan H, Taralp A. In: *Techniques in Protein Chemistry VIII*. Marshak D R. Ed. Section III, pp. 219–230. Academic Press, New York, 1997.
9. Vakos H T, Kaplan H, Black B, Dawson B, Hefford M A. *J. Prot. Chem.* 2000; 19:231.
10. Vakos H T, Black B, Dawson B, Hefford M A, Kaplan H. *J. Prot. Chem.* 2001; 20:521.
11. Yan J X, Sanchez J C, Binz P A, Williams K L, Hochstrasser D F. *Electrophoresis.* 1999; 20:749.
12. Schoellmann G, Shaw E. *Biochemistry* 1963; 2:252.
13. Vath, J E, Zollinger M, Biemann, K. Fresenius Z. *Anal Chem.* 1988; 331:248.

The invention claimed is:

1. A method of detecting peptides, said method comprising the following steps: providing a protein; digesting the protein into at least two peptides; trimethylating amino groups of said peptides under vacuum; and detecting said peptides using mass spectrometry.

2. A method according to claim 1 wherein the amino groups are selected from the group consisting of α-amino and ε-amino.

3. A method according to claim 1 wherein the trimethylated peptides are labeled with different isotopes.

4. A method according to claim 3 wherein the isotopes are selected from the group consisting of $^{12}CH_3$, $^{13}CH_3$ and, $^{12}CD_3$.

5. A method according to claim 1 wherein the mass spectrometry is matrix-assisted laser desorption/ionization mass spectrometry.

6. A method of detecting peptides comprising the following steps: providing a protein having a lysine residue, said lysine residue having an ε-amino group; digesting the protein into at least two peptides; trimethylating said ε-amino group under vacuum: detecting said peptides using mass spectrometry.

7. A method according to claim 6 wherein the trimethylated peptides are labeled with different isotopes.

8. A method according to claim 7 wherein the isotopes are selected from the group consisting of $^{12}CH_3$, $^{13}CH_3$ and, $^{12}CD_3$.

9. A method according to claim 6 wherein the mass spectrometry is matrix-assisted laser desorption/ionization mass spectrometry.

10. A method of detecting peptides comprising the following steps: providing a protein having a lysine residue, said lysine residue having an ε-amino group; digesting the protein into at least two peptides having an α-amino group; trimethylating said α-amino group and ε-amino group under vacuum; detecting said peptides using mass spectrometry.

11. A method according to claim 10 wherein the trimethylated peptides are labeled with two different isotopes.

* * * * *